US006608668B2

(12) United States Patent
Gharib et al.

(10) Patent No.: US 6,608,668 B2
(45) Date of Patent: Aug. 19, 2003

(54) SUB MINIATURIZED LASER DOPPLER VELOCIMETER SENSOR

(75) Inventors: Morteza Gharib, Pasadena, CA (US); Darius Modaress, Pasadena, CA (US); Frederic Taugwalder, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/682,208

(22) Filed: Aug. 6, 2001

(65) Prior Publication Data

US 2002/0075474 A1 Jun. 20, 2002

Related U.S. Application Data

(60) Provisional application No. 60/224,931, filed on Aug. 11, 2000.

(51) Int. Cl.$^7$ ................................................. G01P 3/36
(52) U.S. Cl. ......................................... 356/28; 356/28.5
(58) Field of Search ............................................ 356/28

(56) References Cited

U.S. PATENT DOCUMENTS

| 5,557,396 | A | * | 9/1996 | Ishizuka et al. | ............ 356/28.5 |
| 5,587,785 | A | * | 12/1996 | Kato et al. | .................. 356/28.5 |
| 6,075,600 | A | * | 6/2000 | Nagano et al. | ............. 356/356 |
| 6,323,949 | B1 | * | 11/2001 | Lading et al. | ............. 356/28.5 |

* cited by examiner

*Primary Examiner*—Stephen C. Buczinski
(74) *Attorney, Agent, or Firm*—Fish & Richardson P.C.

(57) ABSTRACT

A miniaturized laser Doppler velocimeter is formed in a housing that is preferably 3 mm in diameter or less. A laser couples light to a first diffractive optical element that is formed on the fiber end. The light is coupled to a lens that also includes a diffractive optical element. The same lens is also used to collect receive light, and receives includes another diffractive optical element to collect that received light.

10 Claims, 1 Drawing Sheet

SUB MINIATURIZED LASER DOPPLER VELOCIMETER SENSOR

CROSS REFERENCE TO RELATED APPLICATIONS

The present application claims priority from application Ser. No. 60/224,931, filed Aug. 11th 2000.

The U.S. government has certain rights in this invention pursuant to Grant No. 30821 awarded by NASA NPO and Grant No. N66001-99-1-8902 awarded by Space and Naval Warfare Systems Center.

BACKGROUND OF INVENTION

Non contact particle sensors are known, and have been described in patents and in the literature. A commercially available laser Doppler velocimeter may include a gas laser and discrete optics. This has often resulted in relatively large and nonportable instruments. The instruments may be unsuitable for harsh environments since they are subject to misalignment.

Diode based laser the velocimeters have been suggested. This may result in miniaturization of the probes and better integration of the structure. Existing probes, however, often require beam alignment for the transmitting optics. This may result in complex optical mechanical system design. This may also be prone to misalignment due to vibration and temperature changes.

SUMMARY OF INVENTION

The present system describes a self-contained rugged sensor probe used for measuring the speed of moving particles and objects that are located at a fixed distance from a housing of the probe. The probe may operate properly without moving parts, and with a minimal number of optical components. The inherent design of the system may operate without calibration, allowing it to be used in hostile environments. The probe may also be sealed and self-contained, allowing more flexibility in its use. For example, ultraviolet and other sterilization techniques may be used when the system is used for biomedical applications.

BRIEF DESCRIPTION OF DRAWINGS

These and other aspects will now be described in detail, with reference to the accompanying drawing, wherein.

DETAILED DESCRIPTION

Figure 1:
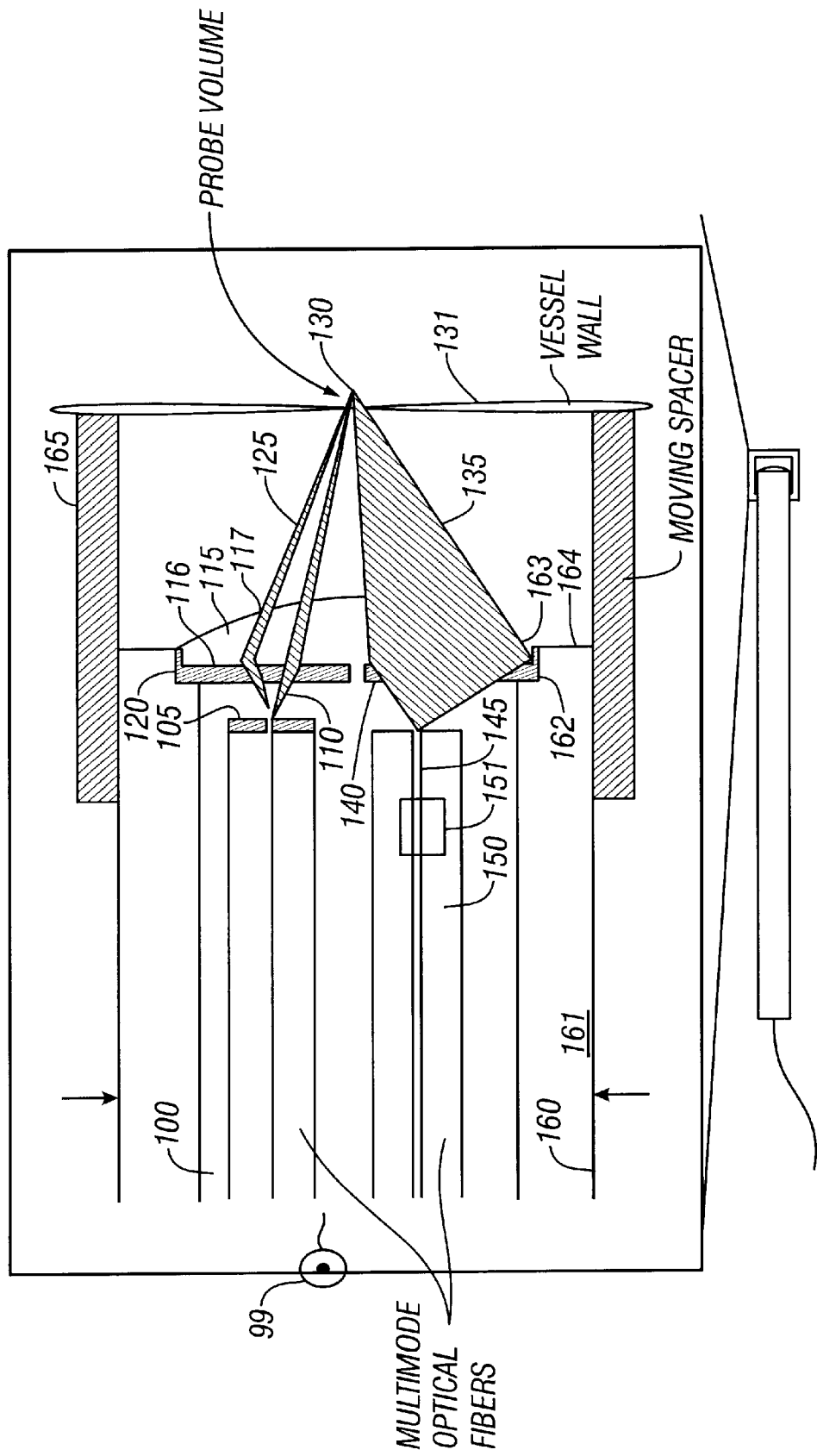
FIG. 1 shows a block diagram type embodiment of the structure of the device.

An embodiment is shown in FIG. 1. This embodiment uses optical fibers and diffractive optical elements to carry out the well-known process of two beam laser Doppler anemometry. This system may allow dramatic minimization of dimensions of the probe and specifically the diameter of the probe.

The present application defines a special way of using optical fibers for injection and collection of light. Light is coupled through a transmitting optical fiber 100 which may be a single-mode optical fiber. The transmitting optical fiber 100 may be driven by any laser of any desired wavelengths. Laser wavelengths between 800 and 1000 nm are often used for biomedical applications. A diffractive optical element 105 is directly written on the distal end portion of the transmitting optical fiber 100. The diffractive optical element can have dimensions and characteristics as disclosed in conventional laser Doppler velocimeter information. The light output 110 from the transmitting optical fiber 100 is coupled to a lens 115 which may be, for example, of focusing lens. In this embodiment, a single lens is used for both transmitting and receiving. An advantage is that the lens can be housed in the housing in a way which extends all the way from one wall of the housing to the other wall of the housing, thus simplifying the formation. For example, a watertight seal may be formed around the edges of the lens in order to seal the housing.

The lens preferably has a flat surface 116, and a curved surface 117 use for the focusing. The portion of the lens which receives that transmitted light from the transmitting optical fiber is marked with a diffractive optical element 120. Therefore, the light output from the transmitting optical fiber 100 is altered by both DOEs. The thus altered light 125 is directed to the probe volume 130.

As described herein, a moving spacer may adjust the distance between the lens the outer surface, and the probe volume.

For example, the probe volume 130 may be directly below the surface of a vessel wall such as a blood vessel.

The light is reflected back from the probe volume 130 as reflected light 135. This light is directed to a second region of the optical lens 115. This second region includes a third diffractive optical element, 140, written thereon. The combination of the lens and third diffractive optical element may effectively focus reflected light 135 to the area of the core 145 of the receiving optical fiber 150. The receiving optical fiber 150 may be a multimode optical fiber.

All of the elements are housed within a housing 160. A housing may be of any shape, and preferably has a maximum outer extent of 3 mm or less. If the housing is cylindrical, which may be preferred, then the housing may have a diameter of 3 mm or less, for example. The outer wall 161 of the housing may be formed from a cylindrical element with a notch 162 that is formed therein. The outer edges of the lens 115 sit within the notch, with of the rear flat surface of the lens also sitting against a surface of the notch 162. As shown, the edge of the front surface of the lens 163 may be substantially aligned with the front surface 164 of the housing element 161. This may be advantageous, since it may allow the front surface of the device to have minimal, if any, edge portions. The front surface of the housing is substantially aligned with edges of the lens.

A second housing element 165 forms a moving spacer that is connected to the first housing element. The moving spacer may fit around the outer surface of the first housing element 161. The connection may be of any type of connection that can allow the moving spacer 165 to move back and forth in the housing. For example, this may be used to tune the location of the probe volume.

The fiber 150 may also optionally include a Bragg grating portion 151 embedded in the fiber optic. This may be used for temperature sensitive measurements as well as reflective, absorption measurements at different wavelengths.

Although only a few embodiments have been disclosed in detail above, other modifications are possible. All such modifications are intended to be encompassed within the following claims, in which:

What is claimed is:

1. An apparatus comprising:
   a housing, having a maximum outer dimension extending from one end to the other, of 3 mm or less; and
   at least an optical transmitter part, and an optical receiver part, and elements which alter the path of light between said optical transmitter part and said optical receiver part, coupled to said housing, and carrying out laser Doppler velocimetry within said housing, wherein said optical transmitter part and said optical receiver par are each formed from lengths of optical fibers, wherein said optical elements include a single lens coupled to both said optical transmitter part and said optical receiver part, wherein said lens has at least one diffractive optical element formed thereon, and wherein said lens has a first flat surface and a second curved surface, and wherein said diffractive optical element is formed on said flat surface.

2. An apparatus comprising:

a housing, having a maximum outer dimension extending from one end to the other, of 3 mm or less; and at least an optical transmitter part, and an optical receiver part, and elements which alter the path of light between said optical transmitter part and said optical receiver part, coupled to said housing, and carrying out laser Doppler velocimetry within said housing wherein said optical transmitter part and said optical receiver part are each formed from lengths of optical if fliers, wherein said optical elements include only a single lens coupled to receive light from both said optical transmitter part and from said optical receiver part wherein said single lens includes a first diffractive optical element part formed thereon adjacent to said optical transmitter part, and a second diffractive optical element formed thereon adjacent to said optical receiver part further comprising a third diffractive optical element, formed on an end of one of said optical fibers.

3. An apparatus as in claim 2, wherein said third diffractive optical element is formed on an end of said fiber that carries out said optical transmitter part.

4. An apparatus comprising:

a housing, having a maximum outer dimension extending from one end to the other, of 3 mm or less; and at least an optical transmitter part, and optical receiver part, and elements which alter the path of light between said optical transmitter part and said optical receiver part, coupled to said housing, and carrying out laser Doppler velocimetry within said housing wherein said optical transmitter part and said optical receiver part are each formed from lengths of optical fibers, wherein said optical transmitter part and said optical receiver part are each formed from lengths of optical fibers, wherein said optical elements include only a single lens coupled to receive light from both said optical transmitter part and from said optical receiver part, further comprising a Bragg element, formed on one of said optical fibers.

5. An apparatus comprising:

a housing;

a first optical fiber within said housing, carrying an optical beam;

a second optical fiber, within said housing, receiving an optical beam that has been reflected from an object of scanning;

a single lens, formed within said housing to cover an entire surface of said housing, to transmit a transmitted optical beam from said first optical fiber, and to receive a reflected optical beam to said second optical fiber, said single lens having a diffractive optical element formed on a surface thereof, wherein said diffractive optical element includes a first portion at an area located to intersect said transmitted optical beam, and a second portion located to intersect a received optical beam, wherein said single lens has a first flat surface facing said first and second optical fibers, and a second curved surface, facing away from said first and second optical fibers.

6. An apparatus as in claim 5, wherein said diffractive optical element is formed on said flat surface of said lens.

7. An apparatus as in claim 6, further comprising another diffractive optical element, formed on a distal surface of said first optical fiber, to intersect said optical beam being carried by said first optical fiber.

8. An apparatus as in claim 7, wherein said housing is substantially cylindrical in shape, and has an outer diameter of approximately 3 mm or less.

9. An apparatus as in claim 7, further comprising a spacer element, coupled around an outside of said optical housing, and holding a front surface of said lens at a specified distance from said object of scanning.

10. An apparatus as in claim 7, further comprising a Bragg optical element, formed as part of said fiber.

* * * * *